US00PP16580P2

(12) United States Plant Patent
Trees

(10) Patent No.: US PP16,580 P2
(45) Date of Patent: May 30, 2006

(54) ***GERANIUM* PLANT NAMED 'BALSHOROFLA'**

(50) Latin Name: *Pelargonium×hortorum*
Varietal Denomination: Balshorofla

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 128 days.

(21) Appl. No.: 11/023,225

(22) Filed: Dec. 27, 2004

(51) Int. Cl.
*A01H 5/00* (2006.01)

(52) U.S. Cl. ..... Plt./328
(58) Field of Classification Search ..... Plt./328
See application file for complete search history.

(56) References Cited

U.S. PATENT DOCUMENTS

PP9,596 P * 6/1996 Trees ..... Plt./325
PP9,765 P * 12/1996 Utecht ..... Plt./325

OTHER PUBLICATIONS

UPOV ROM GTITM Computer Database, GTI Jouve Retrieval Software 2005/02 Citation for 'Balshorofla'.*

* cited by examiner

*Primary Examiner*—Kent Bell
*Assistant Examiner*—W. C. Haas
(74) *Attorney, Agent, or Firm*—Wood, Phillips, Katz, Clark & Mortimer

(57) ABSTRACT

A new and distinct cultivar of *Geranium* plant named 'Balshorofla', characterized by its semi-double pink-colored flowers with darker pink freckle, dark green-colored foliage, and vigorous, upright, and mounded growth habit.

1 Drawing Sheet

Latin name of genus and species of plant claimed: *Pelargonium×hortorum.*
Variety denomination: 'Balshorofla'.

BACKGROUND OF THE INVENTION

The present invention relates to a new and distinct cultivar of *Geranium* plant botanically known as *Pelargonium× hortorum* and hereinafter referred to by the cultivar name 'Balshorofla'.

The new cultivar originated in a controlled breeding program in Arroyo Grande, Calif., during October 2000. The objective of the breeding program was the development of *Geranium* cultivars with an upright mounded growth habit, dark green-colored foliage, and new and unique flower coloration.

The female (seed) parent of the new cultivar was 'Fisbravo', U.S. Plant Pat. No. 9,765, characterized by its pink freckle-colored flowers, medium vigor, and dark green-colored foliage. The male (pollen) parent of the new cultivar was 'Butterfly', not patented, characterized by its lavender-colored flowers, trailing habit, and medium green-colored foliage. The new *Geranium* was discovered and selected by the inventor as a single flowering plant within the progeny of the above stated cross-pollination during March 2001 at Arroyo Grande, Calif.

Asexual reproduction of the new cultivar by terminal stem cuttings since March 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balshorofla' as a new and unique cultivar of *Geranium* plant.

1. Semi-double pink-colored flowers with darker pink freckle.
2. Dark green-colored foliage.
3. Vigorous upright and mounted growth habit.

Plants of the new cultivar differ from plants of the female parent primarily in flower color, number of florets per umbel, and growth vigor and from plants of the male parent primarily in flower color, foliage color, and growth habit.

Of the many commercially available *Geranium* culitvars known to the inventor, the most similar in comparison to the new cultivar is 'BFP-790 Pink Parfait', U.S. Plant Pat. No. 9,596. However, in side by side comparisons, plants of the new cultivar differed from plants of 'BFP-790 Pink Parfait' in the following characteristics:

1. Plants of the new cultivar exhibit darker flower color than plants of 'BFP-790 Pink Parfait'.
2. Plants of the new cultivar exhibit a distinct leaf zonation whereas plants of 'BFP-790 Pink Parfait' do not have leaf zonation.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balshorofla'. The plants were grown for 8 weeks in a greenhouse at West Chicago, Ill.

DETAILED BOTANICAL DESCRIPTION

Figure 1:
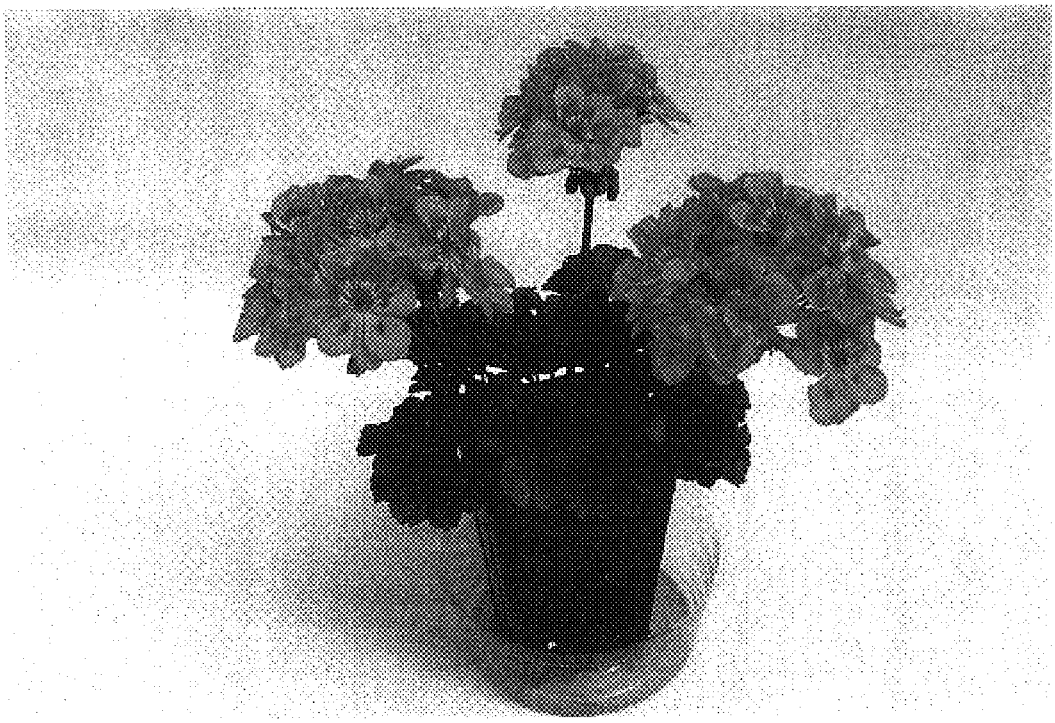
FIG. 1 illustrates a side view of the overall growth and flowering habit of 'Balshorofla'.
Figure 2:
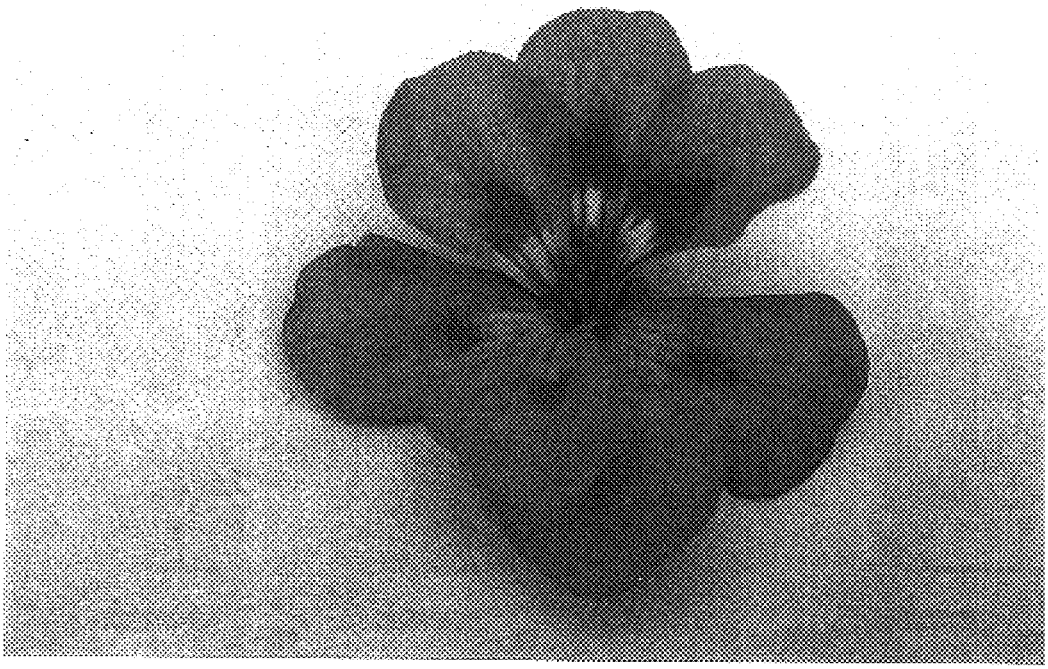
FIG. 2 illustrates a close-up view of a single flower of 'Balshorofla'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 30, 2004 between 10:00 and 11:45 a.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 70° F. (18° C. to 21° C.) during the day and approximately 60° F. to 65° F. (15° C. to 18° C.) during the night. Greenhouse light levels of 4,000–6,000 footcandles were maintained during the day. Plants were pinched at three weeks after the planting of a rooted cutting.

Botanical classification: *Pelargonium×hortorum* cultivar Balshorofla.

Parentage:

*Female parent.*—'Fisbravo', U.S. Plant Pat. No. 9,765.

*Male parent.*—'Butterfly', not patented.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from planting of rooted cutting to finish.

*Growth habit and general appearance.*—Vigorous, upright and mounded.

*Size.*—Height from soil level to top of plant plane: Approximately 18.6 cm. Width/area of spread: Approximately 25.4 cm.

*Branching habit.*—Freely basal branching. Approximately 2 branches per plant.

*Branch.*—Length: Approximately 4.8 cm. Diameter: Approximately 5.1 mm. Texture: Pubescent. Color: 144A. Internode length at center of branch: Approximately 7.6 mm.

*Foliage.*—Number of leaves per lateral branch: Approximately 11. Form: Simple. Arrangement: Opposite. Shape: Reniform. Margin: Crenate. Apex: Rounded. Base: Cordate, open. Venation pattern: Palmate. Upper surface texture: Densely pubescent. Lower surface texture: Moderately pubescent with dense pubescence along veins. Color of upper surface of mature foliage: 147A with veins of 144A and zone darker than 147A. Color of lower surface of mature foliage: Closest to but more yellow than 137A with veins of 144A. Length of mature leaf: Approximately 4.5 cm. Width of mature leaf: Approximately 7.3 cm. Petiole length: Approximately 5.8 cm. Petiole diameter: Approximately 2 mm. Petiole Texture: Pubescent on both upper and lower surface. Petiole color: 146B.

Flowering description:

*Flowering habit.*—'Balshorofla' is freely flowering under outdoor growing conditions with substantially continous blooming from spring through autumn and year round in greenhouse environment.

*Time to first flower.*—Approximately 8 weeks after planting of rooted cutting.

*Lastingness of individual bloom.*—Approximately 5 to 7 days.

Inflorescence description:

*Type.*—Hemispherical umbel. Position: Above foliage. Number of open umbels at any one time: 4. Number of developing umbels at any one time: 2. Umbel diameter: Approximately 9.5 cm. Umbel height/depth: Approximately 7 cm. Number of fully open flowers per umbel: Approximately 12.

*Peduncle.*—Strong, erect. Length: Approximately 12.7 cm. Diameter: Approximately 3.6 mm. Texture: Glandular pubescent. Gland color: Translucent. Color: 144A.

Flower description:

*Bud rate of opening.*—Generally requires 3 to 5 days for bud to progress from first color to fully open flower.

*Bud just before opening.*—Shape: Round. Length: Approximately 1 cm. Diameter: Approximately 7.2 mm. Petal color: N57A. Sepal color: 143B with overlay of 183A at base.

*Corolla.*—Form: Semi-double. Shape: Round, slightly cupped. Diameter/Width: Approximately 4.2 cm. Depth: Approximately 1.5 cm. Fragrance: None. Persistent.

*Petals/petaloids.*—Quantity: Approximately 7 petals and 7 petaloids, of varying shape, per flower. Arrangement: Imbricate. Shape: Obovate. Apex: Obtuse. Base: Attenuate. Margin: Entire. Texture of upper and lower surface: Glabrous. Upper petal length: Approximately 2.4 cm. Upper petal and petaloid width: Approximately 1.6 cm. Upper petal color when fully open: Upper surface: Background of N57C with dusting of N66A, an area of 60A near center of petal and petaloid, and base of 62C with venation of 64A. Lower surface: Gradually fades from 68A at apex to 68C and venation of N66A at base. Lower petal length: Approximately 2.2 cm. Lower petal and petaloid width: Approximately 1.7 cm. Lower petal color, when fully open: Upper surface: N57C with small splotch of N57A in center. Lower surface: Gradually fades from 68A at apex to 68C and venation of N66A at base.

*Pedicel.*—Stength: Strong. Angle: Acute. Length: Approximately 2.5 cm. Diameter: Approximately 0.9 mm. Texture: Moderate soft, short glandular hairs. Gland color: Translucent. Color: 144A.

*Calyx.*—Formed by 5 sepals. Sepal shape: Lanceolate. Sepal apex: Acuminate. Sepal base: Truncate. Sepal margin: Entire. Sepal length: 1.1 cm. Sepal width: 2.3 mm. Texture: Upper surface (inside): Moderate soft, short glandular hairs. Gland color: Translucent. Color: 144A. Sepal color: 144A at apex, 185A at base.

*Reproductive organs.*—Androecium: Stamen number: 9 per flower. Filament color: N155B. Anther shape: Oval. Anther length: Approximately 2 mm. Mature anther color: 186A. Pollen amount: Abundant. Pollen color 168A. Gynoecium: Pistil quantity: One per flower. Pistil length: Approximately 8.9 mm. Stigma shape: 5 pointed star. Stigma length: 1.5 mm. Stigma color: 187C. Style length: 2.8 mm. Style color: 187D. Ovary length: 4.6 mm. Ovary texture: Sericeous. Ovary color: 143C.

Seed and fruit production: Neither seed nor fruit production has been observed.

Disease and pest resistance: Resistance to pathogens and pests common to *geraniums* has not been observed.

What is claimed is:

1. A new and distinct cultivar of *Geranium* plant named 'Balshorofla', substantially as herein shown and described.

* * * * *